(12) United States Patent
Marunaka et al.

(10) Patent No.: US 8,821,926 B2
(45) Date of Patent: Sep. 2, 2014

(54) TABLET CONTAINING HARDLY SOLUBLE ACTIVE INGREDIENT

(75) Inventors: Shigeyuki Marunaka, Osaka (JP); Makoto Fukuta, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1449 days.

(21) Appl. No.: 11/922,769

(22) PCT Filed: Jun. 21, 2006

(86) PCT No.: PCT/JP2006/312419
§ 371 (c)(1),
(2), (4) Date: Dec. 19, 2007

(87) PCT Pub. No.: WO2006/137443
PCT Pub. Date: Dec. 28, 2006

(65) Prior Publication Data
US 2009/0036522 A1    Feb. 5, 2009

(30) Foreign Application Priority Data
Jun. 22, 2005   (JP) ................................. 2005-182415

(51) Int. Cl.
*A61K 9/20* (2006.01)
*A61K 31/34* (2006.01)

(52) U.S. Cl.
USPC ......................................... 424/464; 514/468

(58) Field of Classification Search
USPC ............................................ 424/464; 514/468
See application file for complete search history.

(56) References Cited

U.S. PATENT DOCUMENTS

| 6,034,239 A | 3/2000 | Ohkawa et al. |
| 6,348,485 B1 * | 2/2002 | Ohkawa et al. ............... 514/394 |
| 2004/0018239 A1 | 1/2004 | Ishida et al. |

FOREIGN PATENT DOCUMENTS

| EP | 1 334 732 A1 | 8/2003 | |
| JP | 10-287665 | 10/1998 | |
| JP | 11-322584 | * 11/1999 | ............... A61K 9/16 |
| JP | 2002326927 | 11/2002 | |
| JP | 2006182726 | 7/2006 | |

OTHER PUBLICATIONS

European Search Report for corresponding European Patent Application No. 06767078.6, dated Jul. 10, 2009.

* cited by examiner

*Primary Examiner* — Aradhana Sasan
(74) *Attorney, Agent, or Firm* — Edwards Wildman Palmer LLP; David G. Conlin

(57) ABSTRACT

A tablet showing regulated variation in dissolution from lot to lot which contains from about 3 to about 50% by weight (w/w), based on the whole tablet, of (S)—N-[2-(1,6,7,8-tetrahydro-2H-indeno[5,4-b]furan-8-yl)ethyl]propionamide, magnesium stearate and hydroxypropylcellulose having a viscosity of about 1 to about 4 mPa·s.

1 Claim, 1 Drawing Sheet

TABLET CONTAINING HARDLY SOLUBLE ACTIVE INGREDIENT

CROSS-REFERENCE TO RELATED APPLICATION(S)

This application is a §371 application of copending international patent application PCT/JP2006/312419 which was filed on Jun. 21, 2006, and which claims priority to Japanese Patent Application Serial No. 2005-182415 which was filed on Jun. 22, 2005, both of which are incorporated by reference.

TECHNICAL FIELD

The present invention relates to a tablet, particularly a tablet containing a hardly soluble active ingredient.

BACKGROUND ART

In a tablet containing a hardly soluble active ingredient, a variation arises in dissolution behavior of an active ingredient in some cases. Since this variation is associated with a variation in absorption of the active ingredient, the range of the variation reaching to a certain level or more may result in a variation in efficacy of a medicament as well. In addition, even when there is not such a substantial problem, it is more desirable that there is no variation in quality in products, if at all possible. This is not limited to a medicament, but is also true in all products.

DISCLOSURE OF THE INVENTION

Problems to be Solved by the Invention

The present inventors intensively studied and, as a result, found out that a viscosity of a binder generally used in a tablet is associated with a variation in dissolution behavior of an active ingredient, and further studied, resulting in completion of the present invention.

Means to Solve the Problems

The present invention provides:
[1] a tablet containing from about 3 to about 50% weight (w/w) of a hardly soluble active ingredient based on the whole tablet, magnesium stearate, and hydroxypropylcellulose having a viscosity of about 1 to about 4 mPa·s,
[2] the tablet according to [1], wherein solubility of the hardly soluble active ingredient in water is about 0.005 to about 1 g/L,
[3] the tablet according to [1], wherein the hardly soluble active ingredient is a hardly soluble compound represented by the formula:

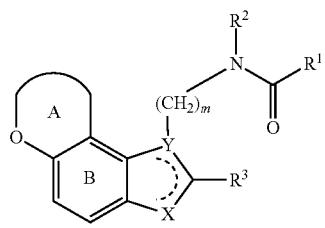

[wherein $R^1$ represents a hydrocarbon group optionally having a substituent, an amino group optionally having a substituent or a heterocyclic group optionally having a substituent, $R^2$ represents a hydrogen atom or a hydrocarbon group optionally having a substituent, $R^3$ represents a hydrogen atom, a hydrocarbon group optionally having a substituent or a heterocyclic group optionally having a substituent, X represents $CHR^4$, $NR^4$, O or S ($R^4$ represents a hydrogen atom or a hydrocarbon group optionally having a substituent), Y represents C, CH or N (provided that when X represents $CH_2$, Y is C or CH), ••• represents a single bond or a double bond, the A ring represents a 5- to 7-membered oxygen atom-containing heterocycle optionally having a substituent, the B ring represents a benzene ring optionally having a substituent, and m represents an integer of 1 to 4]
or a salt thereof,

[4] the tablet according to [1], wherein the hardly soluble active ingredient is (S)—N-[2-(1,6,7,8-tetrahydro-2H-indeno[5,4-b]furan-8-yl)ethyl]propionamide,

[5] a method of regulating variation in dissolution of a hardly soluble active ingredient in a tablet which comprises formulating hydroxylpropylcellulose having a viscosity of 1 to 4 mPa·s into the tablet,

[6] the method according to [5], wherein a similarity factor between preparations with the same formulation in arbitrarily selected different 2 lots, represented by the following equation is 50 to 100:

$$f2 = 50 \log\left\{\left[1 + (1/n)\sum_{t=1}^{n}(At - Bt)^2\right]^{-0.5} \times 100\right\}$$

wherein At and Bt are average dissolution rates of a test preparation A and a test preparation B, respectively, at each dissolution comparison time point, n is the number of the time points at which an average dissolution rate is compared, and is not less than 6, the test preparation A and the test preparation B are preparations with the same formulation in arbitrarily selected different 2 lots, the dissolution comparison time points are set as follows:
(1) when average 85% or more of a hardly soluble active ingredient in the test preparation A is eluted in 15 to 30 minutes: 15, 30, 45 minutes, (2) when average 85% or more of a hardly soluble active ingredient in the test preparation A is eluted after 30 minutes or more but in a defined test time:

Ta/4, 2Ta/4, 3Ta/4, Ta, wherein Ta represents a suitable time point at which the average dissolution rate of the test preparation A attains about 85%, (3) when average 85% or more of a hardly soluble active ingredient in the test preparation A is not eluted in a defined test time:

Ta/4, 2Ta/4, 3Ta/4, Ta, wherein Ta represents a suitable time point at which an dissolution rate attains about 85% of an average dissolution rate of the test preparation A in a defined test time,

[7] a tablet which comprises a hardly soluble active ingredient, magnesium stearate, and hydroxypropylcellulose having a viscosity of about 1 to about 4 mPa·s, and in which variation in dissolution of the hardly soluble active ingredient is regulated,

[8] the tablet according to [1], wherein a similarity factor represented by the following equation is 50 to 100:

$$f2 = 50 \log\left\{\left[1 + (1/n)\sum_{t=1}^{n}(At - Bt)^2\right]^{-0.5} \times 100\right\}$$

wherein At and Bt are average dissolution rates of a test preparation A and a test preparation B, respectively, at each dissolution comparison time point, n is the number of time points at which an average dissolution rate is compared, and is not less than 6, the test preparation A and the test preparation B are preparations with the same formulation in arbitrarily selected different 2 lots, the dissolution comparison time point is set as follows:
(1) when average 85% or more of a hardly soluble active ingredient in the test preparation A is eluted in 15 to 30 minutes: 15, 30, 45 minutes,
(2) when average 85% or more of a hardly soluble active ingredient in the test preparation A is eluted after 30 minutes or more but in a defined test time:
Ta/4, 2Ta/4, 3Ta/4, Ta, wherein Ta represents a suitable time point at which the average dissolution rate of the test preparation A attains about 85%,
(3) when average 85% or more of a hardly soluble active ingredient in the test preparation A is not eluted in a defined test time:
Ta/4, 2Ta/4, 3Ta/4, Ta wherein Ta represents a suitable time point at which an dissolution rate attains about 85% of an average dissolution rate of the test preparation A in a defined test time.

Effect of the Invention

According to the present invention, a tablet showing regulated variation in dissolution of a hardly soluble active ingredient is provided.

BEST MODE FOR CARRYING OUT THE INVENTION

Figure 1:
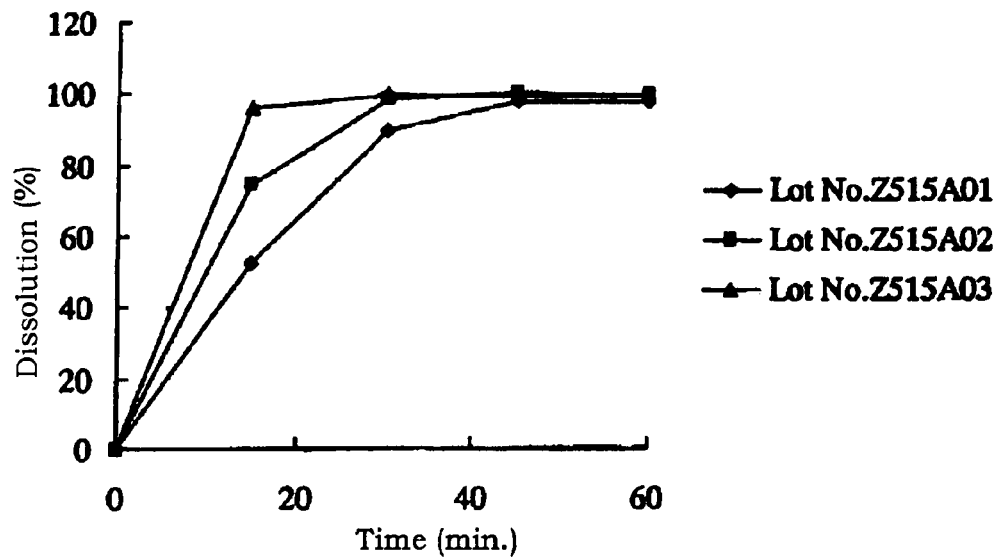
FIG. 1 is a graph showing dissolution behavior of a preparation of Comparative Example.

In the present invention, the term "hardly soluble" means that an active ingredient is hardly soluble in an aqueous solvent such as a body fluid and the like. When the active ingredient is not hardly soluble, originally, a variation in dissolution behavior of the active ingredient is extremely small. Therefore, the present invention is preferably applied to a hardly soluble active ingredient. In the preset description, "hardly soluble" specifically means that solubility in water at 20° C. is about 1 g/l or less. The present invention is more preferably applied to the active ingredient having solubility in water (20° C.) of about 0.7 g/L or less, still more preferably 0.5 g/L or less. An upper limit of a degree of hardly solubility (i.e. lower limit of solubility) is not particularly limited, but the present invention is usually applied to the active ingredient having solubility in water (20° C.) of about 0.005 g/L or more.

The hardly soluble active ingredient herein is a hardly soluble compound represented by the formula (I):

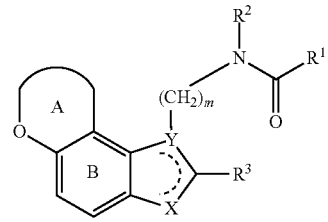

[wherein $R^1$ represents a hydrocarbon group optionally having a substituent, an amino group optionally having a substituent or a heterocyclic group optionally having a substituent, $R^2$ represents a hydrogen atom or a hydrocarbon group optionally having a substituent, $R^3$ represents a hydrogen atom, a hydrocarbon group optionally having a substituent or a heterocyclic group optionally having a substituent, X represents $CHR^4$, $NR^4$, O or S ($R^4$ represents a hydrogen atom or a hydrocarbon group optionally having a substituent), Y represents C, CH or N, ••• represents a single bond or a double bond, an A ring represents a 5- to 7-membered oxygen atom-containing heterocycle optionally having a substituent, a B ring represents a benzene ring optionally having a substituent, and m represents an integer of 1 to 4]
or a salt thereof (hereinafter, simply referred to as a compound of formula (I) in some cases). When X represents $CH_2$, Y is preferably C or CH.

Examples of the "hydrocarbon group" of a term "hydrocarbon group optionally having a substituent" as used herein include an aliphatic hydrocarbon group, a monocyclic saturated hydrocarbon group and an aromatic hydrocarbon group, which preferably have 1 to 16 carbon. Specifically, for example, an alkyl group, an alkenyl group, an alkynyl group a cycloalkyl group and an aryl group are used. As "alkyl group", for example, a lower alkyl group is preferable and, for example, a $C_{1-6}$ alkyl group such as methyl, ethyl, propyl, isopropyl, butyl, isobutyl, sec-butyl and tert-butyl, pentyl and hexyl is generally used. As the "alkenyl group", for example, a lower alkenyl group is preferable, and, for example, a $C_{2-6}$ alkenyl group such as vinyl, 1-propenyl, allyl, isopropenyl, butenyl and isobutenyl is generally used. As the "alkynyl group", for example, a lower alkynyl group is preferable, and, for example, a $C_{2-6}$ alkynyl group such as ethynyl, propargyl and 1-propynyl is generally used. As the "cycloalkyl group", for example, a lower cycloalkyl group is preferable, and, for example a $C_{3-6}$ cycloalkyl group such as cyclopropyl, cyclobutyl, cyclopentyl and cyclohexyl is generally used. As the "aryl group", for example, a $C_{6-14}$ aryl group such as phenyl, 1-naphthyl, 2-naphthyl, biphenylyl and 2-anthryl is preferable, for example, a phenyl group generally is used.

As a substituent which may be possessed by the "hydrocarbon group" of the "hydrocarbon group optionally having a substituent", for example, a halogen atom (e.g. fluorine, chlorine, bromine and iodine), a nitro group, a cyano group, a hydroxy group, an optionally halogenated lower alkyl group (e.g. an optionally halogenated $C_{1-6}$ alkyl group such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl and 6,6,6-trifluorohexyl), a lower alkoxy group (e.g. a $C_{1-6}$ alkoxy group such as methoxy, ethoxy, propoxy, isopropoxy, butoxy, isobutoxy, pentyloxy and hexyloxy), an amino group, a mono-lower alkylamino group (e.g. a mono-$C_{1-6}$ alkylamino group such as methylamino and ethylamino), a di-lower alkylamino group (e.g. a di-$C_{1-6}$ alkylamino group such as dimethylamino and diethylamino), a carboxyl group, a lower alkylcarbonyl group (e.g. a $C_{1-6}$ alkyl-carbonyl group such as acetyl and propionyl), a lower alkoxycarbonyl group (e.g. a $C_{1-6}$ alkoxy-carbonyl group such as methoxycarbonyl, ethoxycarbonyl, propoxycarbonyl and butoxycarbonyl), a carbamoyl group, a mono-lower alkylcarbamoyl group (e.g. a mono-$C_{1-6}$ alkyl-carbamoyl group such as methylcarbamoyl and ethylcarbamoyl), a di-lower alkylcarbamoyl group (e.g. a di-$C_{1-6}$ alkyl-carbamoyl group such as dimethylcarbamoyl and diethylcarbamoyl), an arylcarbamoyl group (e.g. a $C_{6-10}$ aryl-carbamoyl group such as phenylcarbamoyl and naphthylcarbamoyl), an aryl group (e.g. a $C_{6-10}$ aryl group such as phenyl and naphthyl), an aryloxy group (e.g. a $C_{6-10}$ aryloxy group such as phenyloxy and naphthyloxy), an optionally halogenated lower alkylcarbonylamino group (e.g. an optionally halogenated $C_{1-6}$ alkyl-carbonylamino group such as acetylamino and trifluoroacetylamino), and an oxo group are used. The "hydrocarbon group" of the "hydrocarbon group optionally having a substituent" may have 1 to 5, preferably 1 to 3 of the above-described substituents at replaceable positions of the hydrocarbon group and, when the number of substituents is 2 or more, respective substituents may be the same or different.

Examples of the "heterocyclic group" of the term "heterocyclic group optionally having a substituent" as used herein include a 5- to 14-membered (preferably 5- to 10-membered) (monocyclic to tricyclic, preferably monocyclic or dicyclic) heterocyclic group containing 1 to 4 (preferably 1 to 3) of one or two different heteroatoms selected from a nitrogen atom, an oxygen atom and a sulfur atom in addition to carbon atoms. For example, a 5-membered cyclic group containing 1 to 4 heteroatoms selected from an oxygen atom, a sulfur atom and a nitrogen atom in addition to carbon atoms such as 2- or 3-thienyl, 2- or 3-furyl, 1-, 2- or 3-pyrrolyl, 1-, 2- or -3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1,2,3-triazolyl, 1,2,4-triazolyl, 1H- or 2H-tetrazolyl and the like, a 6-membered cyclic group containing 1 to 4 heteroatoms selected from an oxygen atom, a sulfur atom and a nitrogen atom in addition to carbon atoms such as 2-, 3- or 4-pyridyl, N-oxide-2-, 3- or 4-pyridyl, 2-, 4- or 5-pyrimidinyl, N-oxide-2, 4- or 5-pyrimidinyl, thiomorpholinyl, morpholinyl, piperidino, 2-, 3- or 4-piperidyl, thiopyranyl, 1,4-oxadinyl, 1,4-thiadinyl, 1,3-thiadinyl, piperazinyl, triazinyl, 3- or 4-pyridazinyl, pyrazinyl, N-oxide-3- or 4-pyridazinyl and the like, a dicyclic or tricyclic fused cyclic group containing 1 to 4 heteroatoms selected from an oxygen atom, a sulfur atom and a nitrogen atom in addition to carbon atoms such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl, phenoxazinyl and the like (preferably a group formed by fusing the above 5- to 6-membered ring with 1 or 2 of 5- to 6-membered cyclic groups optionally containing 1 to 4 heteroatoms selected from an oxygen atom, a sulfur atom and a nitrogen atom in addition to carbon atoms) and the like are used. Among them, a 5- to 7-membered (preferably 5- or 6-membered) heterocyclic group containing 1 to 3 heteroatoms selected from an oxygen atom, a sulfur atom and a nitrogen atom in addition to carbon atoms is preferable.

As a substituent which may be possessed by "heterocyclic group" of the "heterocyclic group optionally having a substituent", for example, a halogen atom (e.g. fluorine, chlorine, bromine and iodine), a lower alkyl group (e.g. a $C_{1-6}$ alkyl group such as methyl, ethyl, propyl, isopropyl, butyl, isobutyl, sec-butyl, tert-butyl, pentyl, and hexyl), a cycloalkyl group (e.g. a $C_{3-6}$ cycloalkyl group such as cyclopropyl, cyclobutyl, cyclopentyl and cyclohexyl), a lower alkynyl group (e.g. a $C_{2-6}$ alkynyl group such as ethynyl, 1-propynyl and propargyl), a lower alkenyl group (e.g. a $C_{2-6}$ alkenyl group such as vinyl, allyl, isopropenyl, butenyl and isobutenyl), an aralkyl group (e.g. a $C_{7-11}$ aralkyl group such as benzyl, α-methylbenzyl and phenethyl), an aryl group (e.g. a $C_{6-10}$ aryl group such as phenyl and naphthyl, preferably a phenyl group), a lower alkoxy group (e.g. a $C_{1-6}$ alkoxy group such as methoxy, ethoxy, propoxy, isopropoxy, butoxy, isobutoxy, sec-butoxy and tert-butoxy), an aryloxy group (e.g. a $C_{6-10}$ aryloxy group such as phenoxy), a lower alkanoyl group (e.g. formyl; a $C_{1-6}$ alkylcarbonyl group such as acetyl, propionyl, butyryl and isobutyryl), an arylcarbonyl group (e.g. a $C_{1-6}$ aryl-carbonyl group such as a benzoyl group and a naphthoyl group), a lower alkanoyloxy group (e.g. formyloxy; a $C_{1-6}$ alkyl-carbonyloxy group such as acetyloxy, propionyloxy, butyryloxy and isobutyryloxy), an arylcarbonyloxy group (e.g. a $C_{6-10}$ aryl-carbonyloxy group such as benzoyloxy and naphthoyloxy), a carboxyl group, a lower alkoxycarbonyl group (e.g. a $C_{1-6}$ alkoxy-carbonyl group such as methoxycarbonyl, ethoxycarbonyl, propoxycarbonyl, isopropoxycarbonyl, butoxycarbonyl, isobutoxycarbonyl and tert-butoxycarbonyl), an aralkyloxycarbonyl group (e.g. a $C_{7-11}$ aralkyloxycarbonyl group such as benzyloxycarbonyl etc.), a carbamoyl group, a mono-, di- or tri-halogeno-lower alkyl group (e.g. a mono-, di- or tri-halogeno-$C_{1-4}$ alkyl group such as chloromethyl, dichloromethyl, trifluoromethyl and 2,2,2-trifluoroethyl), an oxo group, an amidino group, an imino group, an amino group, a mono-lower alkylamino group (e.g. a mono-$C_{1-4}$ alkylamino group such as methylamino, ethylamino, propylamino, isopropylamino and butylamino), a di-lower alkylamino group (e.g. a di-$C_{1-4}$ alkylamino group such as dimethylamino, diethylamino, dipropylamino, diisopropylamino, dibutylamino and methylethylamino), a 3- to 6-membered cyclic amino group optionally containing 1 to 3 heteroatoms selected from an oxygen atom, a sulfur atom and a nitrogen atom in addition to carbon atoms and one nitrogen atom (e.g. a 3- to 6-membered cyclic amino group such as aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl and N-ethylpiperazinyl), an alkylenedioxy group (e.g. a $C_{1-3}$ alkylenedioxy group such as methylenedioxy and ethylenedioxy), a hydroxy group, a nitro group, a cyano group, a mercapto group, a sulfo group, a sulfino group, a phosphono group, a sulfamoyl group, a monoalkylsulfamoyl group (e.g. mono-$C_{1-6}$ alkylsulfamoyl group such as N-methylsulfamoyl, N-ethylsulfamoyl, N-propylsulfamoyl, N-isopropylsulfamoyl and N-butylsulfamoyl), a dialkylsulfamoyl group (e.g. a di-$C_{1-6}$ alkylsulfamoyl group such as N,N-dimethylsulfamoyl, N,N-diethylsulfamoyl, N,N-dipropylsulfamoyl and N,N-dibutylsulfamoyl), an alkylthio group (e.g. a $C_{1-6}$ alkylthio group such as methylthio, ethylthio, propylthio, isopropylthio, butylthio, sec-butylthio and tert-butylthio), an arylthio group (e.g. a $C_{6-10}$ arylthio group such as phenylthio and naphthylthio), a lower alkylsulfinyl group (e.g. a $C_{1-6}$ alkylsulfinyl group such as methylsulfinyl, ethylsulfinyl, propylsulfinyl and butylsulfinyl), an arylsulfinyl group (e.g. a $C_{6-10}$ arylsulfinyl group such as phenylsulfinyl and naphthylsulfinyl), a lower alkylsulfonyl group (e.g. a $C_{1-6}$ alkylsulfonyl group such as methylsulfonyl, ethylsulfonyl, propylsulfonyl and butylsulfonyl), an arylsulfonyl group (e.g. a $C_{6-10}$ arylsulfonyl group such as phenylsulfonyl and naphthylsulfonyl) are used. The "heterocyclic group" of the "heterocyclic group optionally having a substituent" may have 1 to 5, preferably 1 to 3 of the above-described substituents at replaceable positions of the heterocyclic group and, when the number of substituents is 2 or more, respective substituents may be the same or different.

Examples of the term "amino group optionally having a substituent" as used herein include an amino group optionally having, for example, 1 to 2 of the above-described "hydrocarbon groups optionally having a substituent" as a substituent. A preferable substituent which may be possessed by the "amino group" is, for example, a $C_{1-6}$ alkyl group optionally having a substituent, and a $C_{6-10}$ aryl group optionally having a substituent. As a substituent which may be possessed by the "$C_{1-6}$ alkyl group" or the "$C_{6-10}$ aryl group", the same substituents as those which may be possessed by the "hydrocarbon group" as described above are used. The "lower alkyl group" of a term "lower alkyl group optionally having a substituent" as used herein refers to, for example, a $C_{1-6}$ alkyl group such as methyl, ethyl, propyl, isopropyl, butyl, isobutyl, sec-butyl, and tert-butyl, and may have, for example, 1 to 3 of substituents which may be possessed by the "hydrocarbon group" as described above. The "lower alkoxy group" of the term "lower alkoxy group optionally having a substituent" as used herein refers to, for example, $C_{1-6}$ alkoxy group such as methoxy, ethoxy, propoxy, isopropoxy, butoxy, isobutoxy, sec-butoxy and tert-butoxy and may have, for example, 1 to 3 of substituents which may be possessed by the "hydrocarbon group" as described above.

The term "benzene ring optionally having a substituent" as used herein refers to, for example, a benzene ring optionally having 1 to 2 substituents selected from a halogen atom (e.g. fluorine, chlorine, bromine and iodine), a hydrocarbon group optionally having a substituent, an amino group optionally having a substituent, an amide group (e.g. a $C_{1-3}$ acylamino group such as formamide and acetamide), a lower alkoxy group optionally having a substituent, and a lower alkylenedioxy group (e.g. a $C_{1-3}$ alkylenedioxy group such as methylenedioxy and ethylenedioxy) at replaceable positions. As the "hydrocarbon group optionally having a substituent", the "amino group optionally having a substituent" and the "lower alkoxy group optionally having a substituent", for example, the same groups as those specifically described above are used. When the number of substituents possessed by the "hydrocarbon group", the "amino group" and the "lower alkoxy group" is 2 or more, respective substituents may be the same or different. As the "benzene ring optionally having a substituent", for example, a benzene ring optionally substituted with 1 to 2 substituents selected from a halogen atom (e.g. fluorine, chlorine), a $C_{1-6}$ alkyl group (e.g. methyl, ethyl) and a mono-$C_{1-6}$ alkylamino group is preferable.

In the above formulas, $R^1$ represents a hydrocarbon group optionally having a substituent, an amino group optionally having a substituent or a heterocyclic group optionally having a substituent. As a preferable "hydrocarbon group" of the "hydrocarbon group optionally having a substituent" represented by $R^1$, for example, an alkyl group (e.g. a $C_{1-6}$ alkyl group such as methyl, ethyl, propyl and isopropyl), an alkenyl group (e.g. a $C_{2-6}$ alkenyl group such as vinyl), an alkynyl group (e.g. a $C_{2-6}$ alkynyl group such as ethynyl), a cycloalkyl group (e.g. a $C_{3-6}$ cycloalkyl group such as cyclopropyl, cyclobutyl, cyclopentyl and cyclohexyl) and an aryl group (e.g. a $C_{6-14}$ aryl group such as phenyl), particularly, an alkyl group (e.g. a $C_{1-6}$ alkyl group such as methyl) and a cycloalkyl group (e.g. a $C_{3-6}$ cyclopropyl such as cyclopropyl) are generally used. The "alkyl group", the "alkenyl group", the "alkynyl group", the "cycloalkyl group" and the "aryl group" may have, for example, 1 to 5, preferably 1 to 3 of substituents which may be possessed by "hydrocarbon group" as described above (preferably, a halogen atom such as fluorine).

As a preferable substituent of the "amino group optionally having a substituent" represented by $R^1$, for example, 1 or 2 of a lower alkyl group optionally having a substituent and an aryl group optionally having a substituent are used, particularly, one of a lower alkyl group optionally having a substituent is used. As the "lower alkyl group", for example, a $C_{1-6}$ alkyl group such as methyl, ethyl, propyl, isopropyl, butyl, isobutyl, sec-butyl and tert-butyl is used. The "lower alkyl group" may have, for example, 1 to 3 of substituents that may be possessed by the "hydrocarbon group" as described above. As the "aryl group", for example, a $C_{6-10}$ aryl group such as a phenyl group is used. The "aryl group" may have, for example, 1 to 5, preferably 1 to 3 of substituents that may be possessed by the "hydrocarbon group" as described above (preferably, a halogen atom such as fluorine and chlorine, and a $C_{1-6}$ alkoxy group such as methoxy and ethoxy). As the "amino group optionally having a substituent", for example, a phenylamino group substituted with 1 to 3 of lower alkoxy groups (e.g. a $C_{1-4}$ alkoxy group such as methoxy), or a monoalkylamino group substituted with a lower alkyl group (e.g. a $C_{1-4}$ alkyl group such as methyl, ethyl, propyl, butyl and tert-butyl) is generally used.

As a preferable "heterocyclic group" of the "heterocyclic group optionally having a substituent" represented by $R^1$, for example, a 5- to 6-membered heterocyclic group containing 1 to 3 heteroatoms selected from a nitrogen atom, an oxygen atom and a sulfur atom in addition to carbon atoms is used. Specific examples include 1, 2 or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2-furyl or 3-furyl, pyrazinyl, 2-pyrimidinyl, 3-pyrrolyl, 3-pyridazinyl, 3-isothiazolyl and 3-isoxazolyl. Particularly preferably, a 6-membered nitrogen-containing heterocyclic group (e.g. pyridyl) is used. As a preferable substituent of the heterocyclic group optionally having a substituent" represented by $R^1$, for example, a halogen atom (e.g. chlorine and fluorine), a $C_{1-6}$ alkyl group (e.g. methyl and ethyl), a $C_{1-6}$ alkoxy group (e.g. methoxy and ethoxy), an aralkyloxycarbonyl group (e.g. $C_{7-12}$ aralkyloxy-carbonyl such as benzyloxycarbonyl) and the like are used.

As $R^1$, for example, (i) a lower alkyl group optionally having a substituent, (ii) a lower cycloalkyl group optionally having a substituent, (iii) a lower alkenyl group optionally having a substituent, (iv) an aryl group optionally having a substituent, (v) a mono- or di-lower alkylamino group optionally having a substituent, (vi) an arylamino group optionally having a substituent or (vii) a 5- or 6-membered nitrogen-containing heterocyclic group optionally having a substituent is preferable. As the "lower alkyl group", for example, a $C_{1-6}$ alkyl group such as methyl, ethyl, propyl, isopropyl, butyl, pentyl and hexyl is preferable. As the "lower cycloalkyl group", for example, a $C_{3-6}$ cycloalkyl group such as cyclopropyl, cyclobutyl, cyclopentyl and cyclohexyl is preferable. As the "lower alkenyl group", for example, a $C_{2-6}$ alkenyl group such as vinyl, 1-propenyl and butenyl is preferable. As the "aryl group", for example, a $C_{6-10}$ aryl group such as phenyl, 1-naphthyl and 2-naphthyl is preferable. As the "lower alkylamino group", for example, a mono- or di-$C_{1-6}$ alkylamino group such as methylamino, ethylamino, propylamino, isopropylamino, butylamino, tert-butylamino, dimethylamino, diethylamino and methylethylamino is preferable. As the "arylamino group", for example, a $C_{6-10}$ arylamino group such as phenylamino is preferable. As the "5- or 6-membered nitrogen-containing heterocyclic group", for example, a 5- or 6-membered nitrogen-containing heterocyclic group such as 2-, 3- or 4-pyridyl is preferable. As a substituent that may be possessed by these groups, for example, 1 to 5 substituents which may be possessed by the "hydrocarbon group" as described above are used.

Further preferable examples of $R^1$ include i) a $C_{1-6}$ alkyl group optionally substituted with 1 to 4 of each of halogen or a $C_{1-6}$ alkoxy group, ii) a $C_{3-6}$ cycloalkyl group, iii) a $C_{2-6}$ alkenyl group, iv) a $C_{6-10}$ aryl group optionally substituted with 1 to 4 of each of $C_{1-6}$ alkoxy, nitro, halogeno $C_{1-6}$ alkyl-carbonylamino or halogen atom, v) a mono- or di-$C_{1-6}$ alkylamino group, vi) a $C_{6-10}$ arylamino group optionally substituted with 1 to 3 $C_{1-6}$ alkoxy groups, and vii) a 6-membered nitrogen-containing heterocyclic group optionally substituted with 1 to 2 $C_{7-11}$ aralkyloxycarbonyl groups. Particularly, an optionally halogenated $C_{1-6}$ alkyl group (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, and 6,6,6-trifluorohexyl), a $C_{3-6}$ cycloalkyl group (e.g. cyclopropyl, cyclobutyl, cyclopentyl and cyclohexyl) or a mono-$C_{1-6}$ alkylamino group (e.g. methylamino, ethylamino, propylamino, isopropylamino, butylamino and tert-butylamino) is generally used, and among them, an optionally halogenated $C_{1-6}$ alkyl group or a mono-$C_{1-6}$ alkylamino group, particularly, an optionally halogenated $C_{1-6}$ alkyl group, inter alia, a $C_{1-3}$ alkyl group (e.g. methyl, ethyl and propyl) is preferable.

In the above formula, $R^2$ represents a hydrogen atom or a hydrocarbon group optionally having a substituent. As $R^2$, a hydrogen atom or a lower ($C_{1-6}$) alkyl group optionally having a substituent is preferably used, more preferably, a hydrogen atom or a lower ($C_{1-6}$) alkyl group, particularly, a hydrogen atom is generally used. In the above formula, $R^3$ represents a hydrogen atom, a hydrocarbon group optionally having a substituent or a heterocyclic group optionally having a substituent. As a preferable "hydrocarbon group" of the "hydrocarbon group optionally having a substituent" represented by $R^3$, for example, an alkyl group (e.g. a $C_{1-6}$ alkyl group such as methyl, ethyl, propyl and isopropyl), an alkenyl group (e.g. a $C_{2-6}$ alkenyl group such as vinyl), an alkynyl group (e.g. a $C_{2-6}$ alkynyl group such as ethynyl), and a cycloalkyl group (e.g. a $C_{3-6}$ cycloalkyl group such as cyclopropyl, cyclobutyl, cyclopentyl and cyclohexyl) and an aryl group (e.g. a $C_{6-14}$ aryl group such as phenyl), particularly, an alkyl group (e.g. a $C_{1-6}$ alkyl group such as methyl) and an aryl group (e.g. a $C_{6-14}$ aryl group such as phenyl) are generally used. The "alkyl group", the "alkenyl group", the "alkynyl group", the "cycloalkyl group", and the "aryl group" may have, for example, 1 to 5, preferably 1 to 3 substituents which may be possessed by the "hydrocarbon group" as described above (preferably a halogen atom such as fluorine).

As a preferable "heterocyclic group" of the "heterocyclic group optionally having a substituent" represented by $R^3$, for example, a 5- or 6-membered heterocyclic group containing 1 to 3 heteroatoms selected from a nitrogen atom, an oxygen atom and a sulfur atom in addition to carbon atoms is used. Specifically, examples include 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, and 3-isoxazolyl. Particularly preferably, a 6-membered nitrogen-containing heterocyclic group (e.g. pyridyl) is used. As a preferable substituent of the "heterocyclic group optionally having a substituent" represented by $R^3$, for example, a halogen atom (e.g. chlorine and fluorine), a $C_{1-6}$ alkyl group (e.g. methyl and ethyl), a $C_{1-6}$ alkoxy group (e.g. methoxy and ethoxy), an aralkyloxycarbonyl group (e.g. $C_{7-12}$ aralkyloxy-carbonyl such as benzyloxycarbonyl), an amino group, a mono-$C_{1-6}$ alkylamino group (e.g. methylamino and ethylamino), a di-$C_{1-6}$ alkylamino group (e.g. dimethylamino and diethylamino) are used. $R^3$ is preferably, for example, (i) a hydrogen atom, (ii) a lower alkyl group optionally having a substituent, (iii) an aryl group optionally having a substituent, and (iv) a 5- or 6-membered heterocyclic group optionally having a substituent, and, for example, (i) a hydrogen atom, (ii) a lower alkyl group, (iii) a $C_{6-10}$ aryl group optionally having a substituent, and (iv) a 6-membered nitrogen-containing heterocyclic group optionally having a substituent are more preferable. Examples of the substituent include a halogen atom, a $C_{1-6}$ alkyl group, a $C_{1-6}$ alkoxy group, an amino group, a mono-$C_{1-6}$ alkylamino group and a di-$C_{1-6}$ alkylamino group. More preferably, $R^3$ is a hydrogen atom, a phenyl group, or a 2-, 3- or 4-pyridyl group. Particularly preferably, it is a hydrogen atom.

In the above formula, X represents $CHR^4$, $NR^4$, O or S (wherein $R^4$ represents a hydrogen atom or a hydrocarbon group optionally having a substituent). $X^a$ represents $CHR^{4a}$, $NR^{4a}$, O or S (wherein $R^{4a}$ represents a hydrogen atom or a hydrocarbon group optionally having a substituent). As $R^4$ or $R^{4a}$, a hydrogen atom or a lower ($C_{1-6}$) alkyl group optionally having a substituent is preferable, and a hydrogen atom is generally used. X is preferably $CHR^4$ (wherein $R^4$ is the same as defined above), O or S. Alternatively, X is preferably $CHR^4$ or $NR^4$ (wherein $R^4$ is the same as defined above). $X^a$ is preferably $CHR^{4a}$ or $NR^{4a}$ (wherein $R^{4a}$ is the same as defined above). In the above formula, Y represents C, CH or N. Preferably, it is C or CH. $Y^a$ represents C, CH or N. Preferably, it is C or CH.

In the above formula, the A ring or the A' ring represents a 5- to 7-membered oxygen atom-containing heterocycle optionally having a substituent. Examples of the "5- to 7-membered oxygen atom-containing heterocycle" include 5- to 7-membered (preferably 5- or 6-membered) heterocycle optionally containing 1 to 3 (preferably 1 or 2) of one or two different atoms selected from a nitrogen atom, an oxygen atom and a sulfur atom in addition to hydrocarbon atoms and oxygen atoms. The ring is preferably a ring represented by the formula:

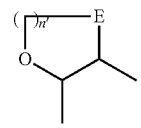

wherein E represents (i) $CH_2CH_2$, (ii) CH=CH, (iii) $CH_2O$, (iv) $OCH_2$, (v) $CH_2S(O)q'$ (wherein q' is an integer of 0 to 2), (vi) $S(O)q'CH_2$ (wherein q' is the same as defined above), (vii) $CH_2NH$, (viii) $NHCH_2$, (ix) N=N, (x) CH=N, (xi) N=CH or (xii) CONH, and n' represents an integer of 0 to 2. E is preferably (i) $CH_2CH_2$, (ii) CH=CH, (iii) $CH_2O$, (iv) $OCH_2$, (v) $CH_2NH$, (vi) $NHCH_2$, (vii) N=N, (viii) CH=N or (ix) N=CH, and especially (i) $CH_2CH_2$ or (ii) CH=CH. Specifically, an oxygen atom-containing 5-membered heterocycle such as 2,3-dihydrofuran, furan, 1,3-dioxol, oxazoline, isoxazole, 1,2,3-oxadiazole and oxazole, and an oxygen atom-containing 6-membered heterocycle such as 2H-3,4-dihydropyran, 2H-pyran, 2,3-dehydro-1,4-dioxane and 2,3-dehydromorpholine are preferable. More preferably the ring is a ring represented by the formula:

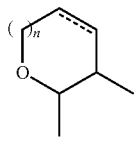

wherein n is the same as defined above. Specifically, for example, 2,3-dihydrofuran, furan, 2H-3,4-dihydropyran, and 2H-pyran are generally used.

As a substituent of the A ring and the A' ring, for example, a halogen atom (e.g. fluorine, chlorine, bromine and iodine), a lower alkyl group optionally having a substituent, a cycloalkyl group optionally having a substituent, a lower alkynyl group optionally having a substituent, a lower alkenyl group optionally having a substituent, an aryl group optionally having a substituent, a lower alkoxy group (e.g. a $C_{1-6}$ alkoxy group such as methoxy, ethoxy, propoxy, isopropoxy, butoxy, isobutoxy, sec-butoxy and tert-butoxy), an aryloxy group (e.g. a $C_{6-10}$ aryloxy group such as phenoxy), a lower alkanoyl group (e.g. formyl; a $C_{1-6}$ alkyl-carbonyl group such as acetyl, propionyl, butyryl and isobutyryl), an arylcarbonyl group (e.g. a $C_{6-10}$ aryl-carbonyl group such as a benzoyl group and a naphthoyl group), a lower alkanoyloxy group (e.g. formyloxy; a $C_{1-6}$ alkyl-carbonyloxy group such as acetyloxy, propionyloxy, butyryloxy and isobutyryloxy), an arylcarbonyloxy group (e.g. a $C_{6-10}$ aryl-carbonyloxy group such as benzoyloxy and naphthoyloxy), a carboxyl group, a lower alkoxycarbonyl group (e.g. a $C_{1-6}$ alkoxy-carbonyl group such as methoxycarbonyl, ethoxycarbonyl, propoxycarbonyl, isopropoxycarbonyl, butoxycarbonyl, isobutoxycarbonyl and tert-butoxycarbonyl), an aralkyloxycarbonyl (e.g. a $C_{7-11}$ aralkyloxy-carbonyl group such as benzyloxycarbonyl), a carbamoyl group, a mono-, di- or tri-halogeno-lower alkyl group (e.g. a mono-, di- or tri-halogeno-$C_{1-4}$ alkyl group such as chloromethyl, dichloromethyl, trifluoromethyl and 2,2,2-trifluoroethyl), an oxo group, an amidino group, an imino group, an amino group, a mono-lower alkylamino group (e.g. a mono-$C_{1-4}$ alkylamino group such as methylamino, ethylamino, propylamino, isopropylamino and butylamino), a di-lower alkylamino group (e.g. a di-$C_{1-4}$ alkylamino group such as dimethylamino, diethylamino, dipropylamino, diisopropylamino, dibutylamino and methylethylamino), a 3- to 6-membered cyclic amino group optionally containing 1 to 3 heteroatoms selected from an oxygen atom, a sulfur atom and a nitrogen atom in addition to carbon atoms and one nitrogen atom (e.g. a 3- to 6-membered cyclic amino group such as aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl and N-ethylpiperazinyl), an alkylenedioxy group (e.g. a $C_{1-3}$ alkylenedioxy group such as methylenedioxy and ethylenedioxy), a hydroxy group, a nitro group, a cyano group, a mercapto group, a sulfo group, a sulfino group, a phosphono group, a sulfamoyl group, a monoalkylsulfamoyl group (e.g. a mono-$C_{1-6}$ alkylsulfamoyl group such as N-methylsulfamoyl, N-ethylsulfamoyl, N-propylsulfamoyl, N-isopropylsulfamoyl and N-butylsulfamoyl), a dialkylsulfamoyl group (e.g. a di-$C_{1-6}$ alkylsulfamoyl group such as N,N-dimethylsulfamoyl, N,N-diethylsulfamoyl, N,N-dipropylsulfamoyl and N,N-dibutylsulfamoyl), an alkylthio group (e.g. a $C_{1-6}$ alkylthio group such as methylthio, ethylthio, propylthio, isopropylthio, butylthio, sec-butylthio and tert-butylthio), an arylthio group (e.g. a $C_{6-10}$ arylthio group such as phenylthio and naphthylthio), a lower alkylsulfinyl group (e.g. a $C_{1-6}$ alkylsulfinyl group such as methylsulfinyl, ethylsulfinyl, propylsulfinyl and butylsulfinyl), an arylsulfinyl group (e.g. a $C_{6-10}$ arylsulfinyl group such as phenylsulfinyl and naphthylsulfinyl), a lower alkylsulfonyl group (e.g. a $C_{1-6}$ alkylsulfonyl group such as methylsulfonyl, ethylsulfonyl, propylsulfonyl and butylsulfonyl), and an arylsulfonyl group (e.g. a $C_{6-10}$ arylsulfonyl group such as phenylsulfonyl and naphthylsulfonyl) are used. The "lower alkyl group", the "lower alkenyl group", the "lower alkynyl group", the "lower cycloalkyl group", and the "aryl group" may have, 1 to 5, preferably 1 to 3 substituents which may be possessed by the "hydrocarbon group" as described above.

Preferable substituents of the A ring and the A' ring include a halogen atom, a $C_{1-6}$ alkyl group optionally having a substituent, a $C_{1-6}$ alkoxy group optionally having a substituent, a hydroxyl group, a nitro group, a cyano group, an amino group optionally having a substituent, and an oxo group. The "substituent" of the "$C_{1-6}$ alkyl group optionally having a substituent", the "$C_{1-6}$ alkoxy group optionally having a substituent", and the "amino group optionally having a substituent" represents, for example, substituents that may be possessed by the "hydrocarbon group" as described above. The A ring and the A' ring may have 1 to 4, preferably 1 or 2 of the above-described substituents at replaceable positions depending on a size of the ring and, when the number of substituents is 2 or more, respective substituents may be the same or different. Examples of the A ring and the A' ring include, for example,

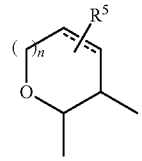

wherein n is as the same defined above, and $R^5$ represents a hydrogen atom or 1 or 2 substituents described as the "preferable substituents of the A ring and the A' ring". Among them, the ring wherein $R^5$ is a hydrogen atom, or a $C_{1-6}$ alkyl group optionally having a substituent, particularly, $R^5$ is a hydrogen atom (an unsubstituted A ring and an unsubstituted A' ring) is generally used.

In the above formula, the B ring represents a benzene ring optionally having a substituent. The substituent of the B ring includes, for example, "substituents" of the "benzene ring optionally having a substituent" as described above. Among them, a halogen atom or a lower ($C_{1-6}$) alkyl group optionally having a substituent is preferable and, particularly, a halogen atom or a lower ($C_{1-6}$) alkyl group (preferably methyl) is generally used. The "substituent" of the "lower ($C_{1-6}$) alkyl group optionally having a substituent" represents, for example, substituents that may be possessed by the "hydrocarbon group" as described above. The B ring may have 1 or 2, preferably 1 of the substituents at replaceable positions and, when the number of substituents is 2, respective substituents may be the same or different. Preferably, the B ring is, for example,

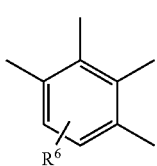

wherein R⁶ represents a hydrogen atom, a halogen atom, a lower ($C_{1-6}$) alkyl group optionally having a substituent or a lower ($C_{1-6}$) alkoxy group optionally having a substituent. R⁶ is preferably, for example, a hydrogen atom, a halogen atom or a lower ($C_{1-6}$)alkyl group (preferably methyl). More preferably, it is a hydrogen atom.

In the above formula, m represents an integer of 1 to 4. Preferably, m is an integer of 1 to 3. More preferably, m is 2 or 3, particularly, m is preferably 2. In the above formula, n represents an integer of 0 to 2. Preferably, n is an integer of 0 or 1. Particularly, n is preferably 0.

Examples of

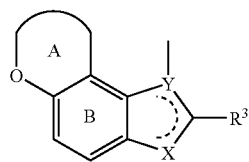

include

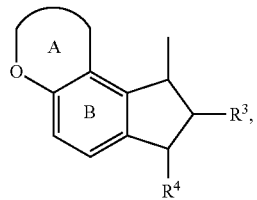 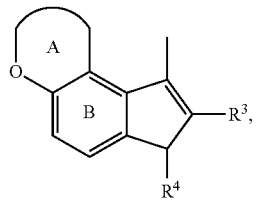

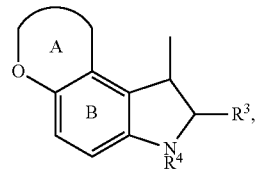 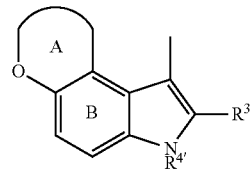

wherein R⁴' represents a hydrocarbon group optionally having a substituent, and other respective symbols are the same as defined above. Preferably, R⁴' is lower ($C_{1-3}$) alkyl optionally having a substituent.

As preferable examples of

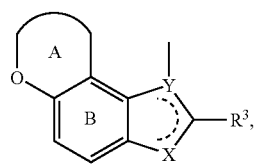 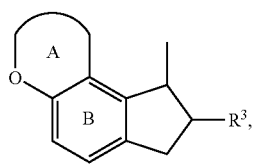

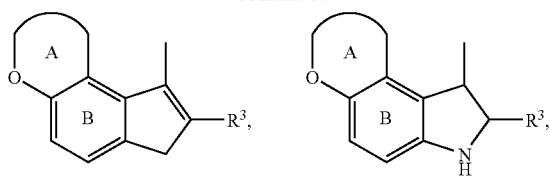

wherein respective symbols are the same as defined above are exemplified. Among them,

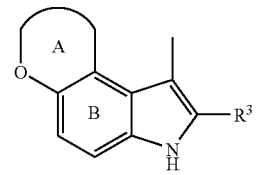

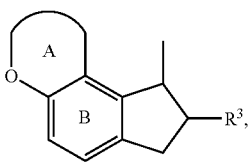 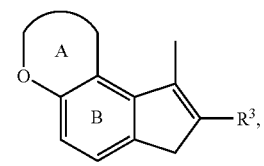

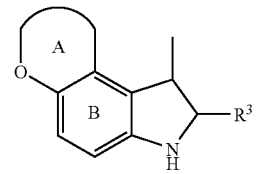

wherein respective symbols are the same as defined above are preferred.

In addition, (i)

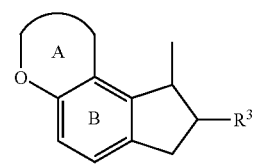 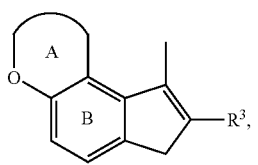

(ii)

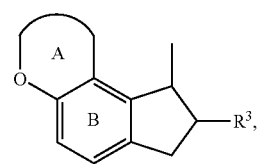 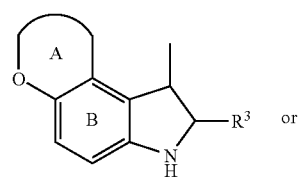 or (iii)

wherein respective symbols are the same as defined above are preferably used. Among them,

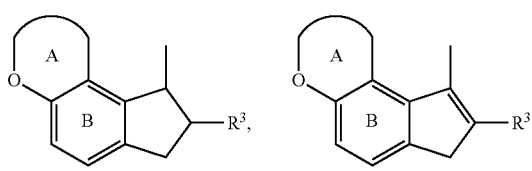

wherein respective symbols are the same as defined above are preferred. Particularly,

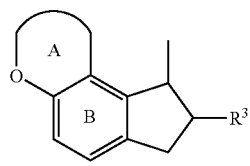

wherein respective symbols are the same as defined above is preferred.

Examples of

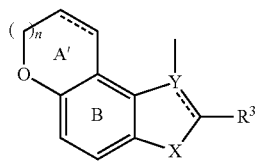

include

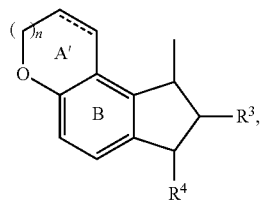 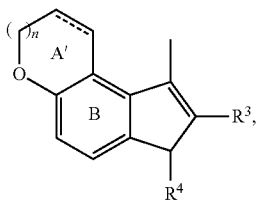

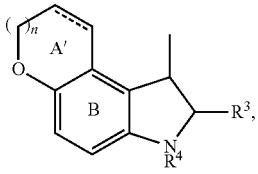 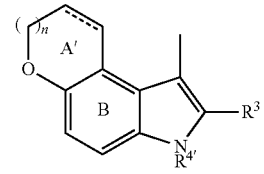

wherein respective symbols are the same as defined above.

As preferable examples of

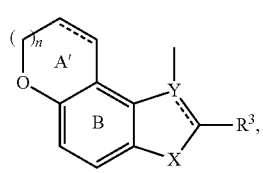 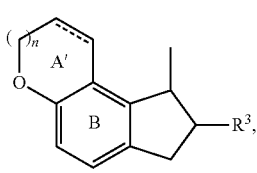

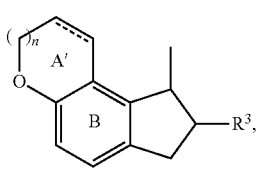 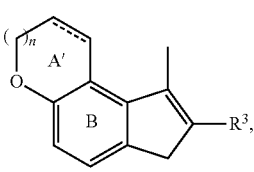

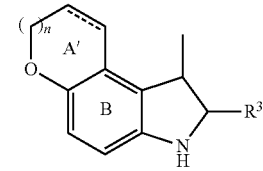

wherein respective symbols are the same as defined above are exemplified. Among them,

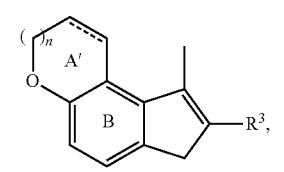

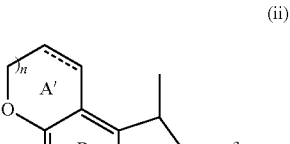

wherein respective symbols are the same as defined above is preferred.

In addition, (i)

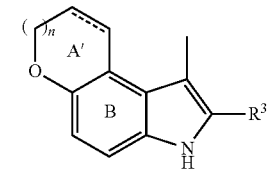

(ii)

(iii)

wherein respective symbols are the same as defined above are preferably used. Among them,

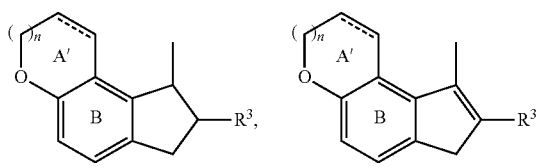

wherein respective symbols are the same as defined above are preferred. Further,

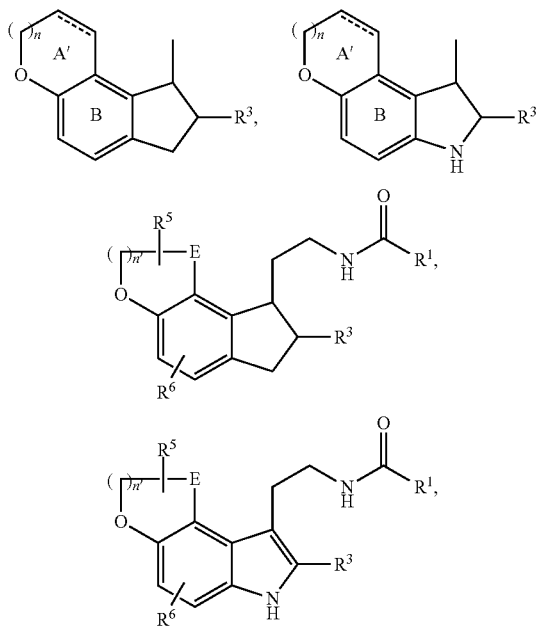

wherein respective symbols are the same as defined above are also preferred. Particularly,

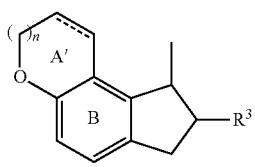

wherein respective symbols are the same as defined above is preferred.

As the compound (I) of the present invention, for example, compounds having the following structural formulas:

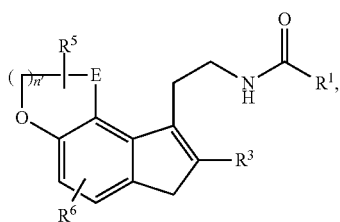

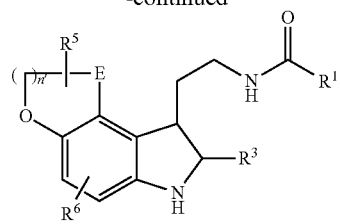

wherein respective symbols are the same as defined above are particularly generally used.

Preferable examples of the compound (I) include compounds represented by the formulas:

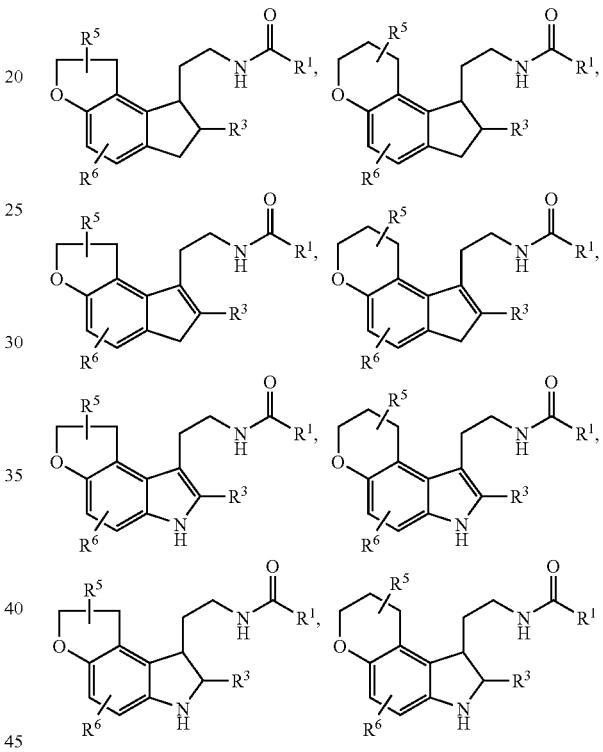

wherein respective symbols are the same as defined above.

In addition, preferable examples of the compound (I) include a compound in which $R^1$ represents (i) a lower alkyl group optionally having a substituent, (ii) a lower cycloalkyl group optionally having a substituent, (iii) a lower alkenyl group optionally having a substituent, (iv) an aryl group optionally having a substituent, (v) a mono- or di-lower alkylamino group optionally having a substituent, (vi) an arylamino group optionally having a substituent or (vii) a 5- or 6-membered nitrogen-containing heterocyclic group optionally having a substituent, $R^2$ represents a hydrogen atom or a lower ($C_{1-6}$) alkyl group optionally having a substituent, $R^3$ represents (i) a hydrogen atom, (ii) a lower alkyl group optionally having a substituent or (iii) an aryl group optionally having a substituent, X represents $CHR^4$ or $NR^4$ ($R^4$ represents a hydrogen atom or a lower ($C_{1-6}$) alkyl group optionally substituted with an oxo group), Y represents C, CH or N (provided that, when X represents $CH^2$, Y is C or CH), ••• represents a single bond or a double bond, an A ring represents a 5- to 7-membered oxygen atom containing heterocycle optionally having a substituent, a B ring represents a benzene ring optionally having a substituent, and m is 1 or 2.

More preferably, the compound is a compound in which $R^1$ represents i) a $C_{1-6}$ alkyl group optionally substituted with 1 to 4 of each of halogen or a $C_{1-6}$ alkoxy group, ii) a $C_{3-6}$ cycloalkyl group, iii) a $C_{2-6}$ alkenyl group, iv) a $C_{6-10}$ aryl group optionally substituted with 1 to 4 of each of $C_{1-6}$ alkoxy, nitro, halogeno $C_{1-6}$ alkyl-carbonylamino or a halogen atom, v) a mono- or di-$C_{1-6}$ alkylamino group, vi) a $C_{6-10}$ arylamino group optionally substituted with 1 to 3 $C_{1-6}$ alkoxy groups or vii) a 6-membered nitrogen-containing heterocyclic group optionally substituted with 1 to 2 $C_{7-11}$ aralkyloxy-carbonyl groups, $R^2$ represents a hydrogen atom or a lower ($C_{1-6}$) alkyl group, $R^3$ represents (i) a hydrogen atom, (ii) a lower ($C_{1-6}$) alkyl group, or (iii) a $C_{6-14}$ aryl group, X represents $CHR^4$ or $NR^4$ (wherein $R^4$ represents a hydrogen atom or a lower ($C_{1-6}$) alkyl group optionally substituted with an oxo group), Y represents C, CH or N (provided that, when X represents $CH_2$, Y is C or CH), ••• represents a single bond or a double bond,
an A ring represents:

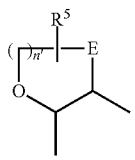

wherein respective symbols are the same as defined above,
a B ring represents:

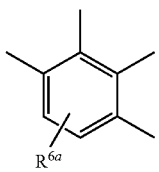

$R^{6a}$ represents a hydrogen atom, a halogen atom or a lower ($C_{1-6}$)alkyl group, and
m is 1 or 2.

Among them, a compound represented by the formula:

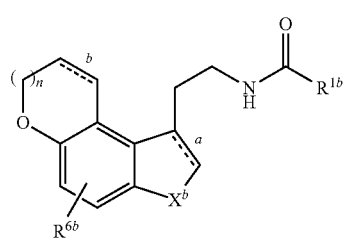

wherein $R^{1b}$ represents a $C_{1-6}$ alkyl group, $R^{6b}$ represents a hydrogen atom or a halogen atom, n is 0 or 1, $$\overset{b}{=====}$$

represents a single bond or a double bond, and when $X^b$ is $CH_2$, $$\overset{a}{=====}$$

represents a single bond or a double bond, and when $X^b$ is NH, $$\overset{a}{=====}$$

represents a single bond or a salt thereof is preferred.

In addition, a compound represented by the formula:

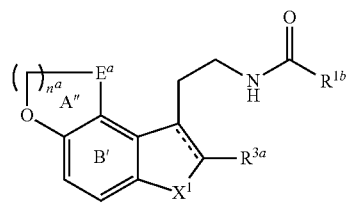

wherein $R^{1b}$ represents a $C_{1-6}$ alkyl group,
X' represents $CH_2$, NH or NCHO,
$R^{3a}$ represents a hydrogen atom or a phenyl group,
••• represents a single bond or a double bond,
Ea represents $CH_2CH_2$, CH=CH, $CH_2O$, CH=N, CONH or $CH_2NH$,
$n^a$ represents 0 or 1,
an A" ring represents an oxygen atom-containing 5- or 6-membered heterocycle optionally having 1 or 2 $C_{1-6}$ alkyl groups optionally substituted with a hydroxyl group, and a B' ring represents a benzene ring optionally substituted with a halogen atom or a salt thereof is also preferred. Among them, a compound in which when X' is $CH_2$ or NCHO,
••• is a single bond or a double bond, and when X' is NHO,
••• is a single bond, or a salt thereof is also preferred.

The compound (I) is particularly preferably (S)—N-[2-(1,6,7,8-tetrahydro-2H-indeno[5,4-b]furan-8-yl)ethyl]propionamide (general name: Ramelteon) (hereinafter referred to as Compound A in some cases).

The compound (I) is the known compound useful as an agent for preventing or treating sleep disorder, described in JP-A-10-287665, and can be produced according to the known methods such as the method described in the publication or the like.

The tablet of the present invention contains about 3% by weight (w/w) or more of such a hardly soluble active ingredient based on the whole tablet. When a content of the hardly soluble active ingredient is less than this amount, originally, a variation in dissolution behavior of the active ingredient is extremely small in the tablet. The tablet of the present invention contains such a hardly soluble active ingredient in an amount of preferably about 5% by weight (w/w) or more, more preferably about 7% by weight (w/w) or more, particularly preferably about 10% by weight (w/w) or more. In addition, a content of the hardly soluble active ingredient in the tablet of the present invention is usually not more than about 50% by weight (w/w).

The tablet of the present invention contains magnesium stearate. Magnesium stearate is a general-use lubricant, and is available as a commercial product. Such a commercially available product of magnesium stearate usually contains components other than magnesium stearate. In the present invention, from a viewpoint of regulated variation in dissolution of an active ingredient and improvement in a rate of the dissolution, magnesium stearate in which the proportion of stearic acid in a fatty acid fraction (the stearic acid content ratio) values about 90% or more is suitably used. The stearic acid content ratio is calculated according to the method described in the Japanese Pharmacopoeia, 14th Edition. The tablet of the present invention preferably contains magnesium stearate in an amount of about 0.7% by weight (w/w) or more based on the whole tablet. The upper limit of the magnesium stearate content is not particularly limited, but usually is not more than about 2% by weight (w/w) based on the whole tablet.

The tablet of the present invention contains hydroxylpropylcellulose having a viscosity of about 1 to about 4 mPa·s (preferably viscosity of about 2 to about 3.4 mPa·s). Hydroxpropylcellulose is a general-use binder, and usually, when it is used as a binder for the tablet, hydroxypropylcellulose having a higher viscosity is used. The present invention is characterized in that hydroxypropylcellulose having a relatively low viscosity is used.

Such hydroxypropylcellulose is available, for example, as a commercially available product (e.g. SSL type, SL type, Nippon Soda Co., Ltd.).

Inter alia, hydroxypropylcellulose having a low mineral obtained by repetition of purification is preferred, and hydroxypropylcellulose having a residue on ignition of not more than about 0.2% as measured after ignition at 600±50° C. is preferred. Further, hydroxypropylcellulose which is soluble in water and a polar organic solvent such as an alcohol at normal temperature and has greater solubility in water is preferred.

In the present specification, a numerical value of a viscosity is a numerical value of a viscosity as measured using a 2% Aqueous Solution Type B Viscometer at 20° C.

The tablet of the present invention preferably contains about 3% by weight (w/w) of such a hydroxypropylcellulose based on the whole tablet.

The tablet of the present invention may optionally contain other active ingredients, and other components such as other additives.

The tablet of the present invention can be produced by mixing a hardly soluble active ingredient, magnesium stearate, and hydroxypropylcellulose having a viscosity of about 1 to about 4 mPa·s as well as other optionally incorporated components at a predetermined ratio, and compressing the mixture to tablets according to a normal method which is used for preparation.

More specifically, the tablet can be produced, for example, by the following method.

After a hardly soluble active ingredient and optionally incorporated components (excipient, etc.) are homogeneously mixed in a fluidized bed granulation dryer, the mixture is sprayed with an aqueous solution in which hydroxypropylcellulose having a viscosity of about 1 to about 4 mPa·s is dissolved to granulate in the dryer, and then, dried in the same dryer.

The resultant granules are ground to obtain a particle size-adjusted powder.

Magnesium stearate and optionally incorporated components (disintegrating agent, etc.) are added to the particle size-adjusted powder, and mixed to obtain granules for making tablet.

The granules are compressed into a tablet on a tablet press to obtain an uncoated tablet.

The resultant uncoated tablet is sprayed with a film coating solution in a film coating device to obtain a film coated tablet.

According to the present invention, since an dissolution rate of a hardly soluble active ingredient is improved, and the dissolution rate is converged to an approximate defined value, the tablet of the present invention has a regulated dissolution variation of a hardly soluble active ingredient. In the present specification, the regulated dissolution variation means that a similarity factor (f2 function) which is an index for assessing equality of dissolution behavior between preparations with the same formulation in arbitrarily selected different 2 lots is 50 to 100. The similarity factor (f2 function) is preferably 70 to 100.

The same formulation means that names and amounts of components to be incorporated are substantially the same, and lots of components to be incorporated may be the same or different.

The similarity factor is expressed by the following equation.

$$f2 = 50 \log\left\{\left[1 + (1/n)\sum_{t=1}^{n}(At - Bt)^2\right]^{-0.5} \times 100\right\} \quad \text{Equation}$$

wherein At and Bt are average dissolution rates of a test preparation A and a test preparation B, respectively, at each dissolution comparison time point, n is the number of the time points at which an average dissolution rate is compared, and is not less than 6, the test preparation A and the test preparation B are preparations with the same formulation in arbitrarily selected different 2 lots, the dissolution comparison time points are set as follows:
(1) when average 85% or more of a hardly soluble active ingredient in the test preparation A is eluted in 15 to 30 minutes: 15, 30, 45 minutes,
(2) when average 85% or more of a hardly soluble active ingredient in the test preparation A is eluted after 30 minutes or more but in a defined test time:
Ta/4, 2Ta/4, 3Ta/4, Ta, wherein Ta represents a suitable time point at which the average dissolution rate of the test preparation A attains about 85%,
(3) when average 85% or more of a hardly soluble active ingredient in the test preparation A is not eluted in a defined test time:
Ta/4, 2Ta/4, 3Ta/4, Ta, wherein Ta represents a suitable time point at which an average dissolution rate attains about 85% of an average dissolution rate of the test preparation A in a defined test time.

The tablet of the present invention can be orally administered according to the usual tablet administration regimen.

Specifically, for example, 4 to 16 mg of a hardly soluble active ingredient can be orally administered once a day before going to bed.

EXAMPLES

The represent invention will be described in more detail by the following Reference Examples and Examples, but the present invention is not limited thereto.

In the following Examples, as hydroxypropylcellulose (viscosity of 2 to 3.4 mPa·s), 1 to 2 g of hydroxypropylcellulose that is precisely weighted, and has a residue on ignition of not more than 0.2% as measured after ignition at 600±50° C. was used.

In the following Examples and Comparative Examples, as a preparation additive, products which meet the Japanese Pharmacopoeia, 14th Edition or the Pharmaceutical Excipients Standards 2003 were used, provided that among preparation additives, as magnesium stearate, products which meet the Japanese Pharmacopoeia, 14th Edition is used in the same manner as other preparation additives, and particularly, magnesium stearate having a stearic acid content ratio of about 90% or more (TAIHEI CHEMICAL INDUSTRIAL CO., LTD.) was used.

Reference Example 1

After Compound A, lactose and corn starch were homogeneously mixed in a fluidized bed granulation dryer according to the formulation in Table 1, the mixture was sprayed with an aqueous solution in which hydroxypropylcellulose had been dissolved to granulate in the dryer, and then, dried in the same dryer. The resultant granules were ground with a 1.5 mmφ punching screen using a power mill to obtain a particle size-adjusted powder. Corn starch and magnesium stearate were added to the particle size-adjusted powder, and mixed in a tumbler mixer to obtain granules for making tablet. The granules were compressed into a tablet weighing 130 mg on a tablet press using a 7.0 mmφ mallet to obtain an uncoated tablet. The resulting uncoated tablet was sprayed with a solution of titanium oxide, hydroxypropylmethylcellulose 2910 in which yellow iron sesquioxide had been dispersed, and copolyvidone in a film coating device to obtain each about 270000 film coated tablets containing 4 mg or 8 mg of Compound A per tablet.

TABLE 1

|  | 4 mg | 8 mg |
|---|---|---|
| Uncoated tablet | | |
| Compound A | 4.0 | 8.0 |
| Lactose | 101.6 | 97.6 |
| Corn starch | 19.4 | 19.4 |
| Hydroxypropylcellulose (viscosity 6 to 10 mPa · s) | 4.0 | 4.0 |
| Magnesium stearate | 1.0 | 1.0 |
| Film coating | | |
| Hydoxypropylmethylcellulose 2910 | 3.75 | 3.74 |
| Copolyvidone | 0.75 | 0.75 |
| Titanium oxide | 0.5 | 0.5 |
| Yellow iron oxide | — | 0.01 |
| Total | 135.0 | 135.0 |

Example 1

After Compound A, lactose and corn starch were homogeneously mixed in a fluidized bed granulation dryer according to the formulation of Table 2, the mixture was sprayed with an aqueous solution in which hydroxypropylcellulose had been dissolved to granulate in the dryer, and then, dried in the same dryer. The resultant granules were ground with a 1.5 mmφ punching screen using a power mill to obtain a particle size-adjusted powder. Corn starch and magnesium stearate were added to this size-adjusted powder, and mixed in a tumbler mixer to obtain granules for making tablet. The granules were compressed into a tablet weighing 130 mg on a tablet press using a 7.0 mmφ mallet to obtain a uncoated tablet. The resulting uncoated plain tablet was sprayed with a solution of titanium oxide, hydroxypropylmethylcellulose 2910 in which yellow iron oxide or red iron oxide had been dispersed, and copolyvidone in a film coating device to obtain film coated tablets of Preparation A (Comparative Example) and Preparation B (Example) containing 16 mg of Compound A per tablet. The procedure was repeated three times to obtain each 3 lots of preparations (Preparation A: Lot No. Z515A01, Lot No. Z515A02, Lot No. Z515A03) (Preparation B: Lot No. Z515G01, Lot No. Z515G02, Lot No. Z515G03).

TABLE 2

|  | Preparation A (Comparative Example) | Preparation B (Example) |
|---|---|---|
| Uncoated tablet | | |
| Compound A | 16.0 | 16.0 |
| Lactose | 89.6 | 89.6 |
| Cone starch | 19.4 | 19.4 |
| Hydroxypropylcellulose (viscosity 6 to 10 mPa · s) | 4.0 | |
| Hydroxypropylcellulose (viscosity 2 to 3.4 mPa · s) | | 4.0 |
| Magnesium stearate | 1.0 | 1.0 |
| Film coating | | |
| Hydroxypropylmethylcellulose 2910 | 3.74 | 3.74 |
| Copolyvidone | 0.75 | 0.75 |
| Titanium oxide | 0.5 | 0.5 |
| Yellow iron sesquioxide | 0.01 | — |
| Iron sesquioxide | — | 0.01 |
| Total | 135.0 | 135.0 |

Test Example 1

Figure 2:
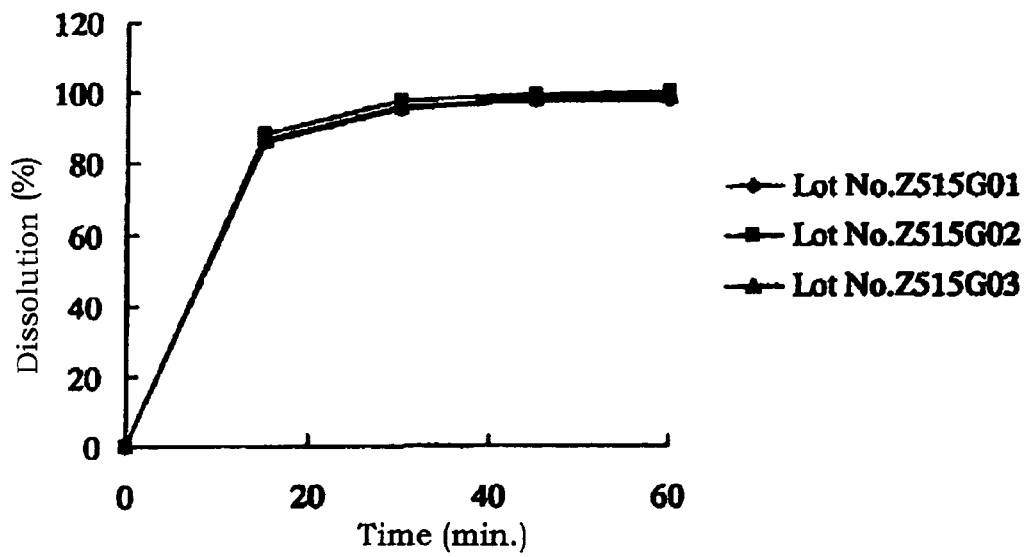
FIG. 2 is a graph showing dissolution behavior of a preparation of Example.

According to the paddle method in the Japanese Pharmacopoeia (50 rpm, 37° C., 900 mL of water, n=6), the dissolution behavior of Compound A in each 3 lots of Preparation A (Comparative Example) and Preparation B (Example) was measured. Results are shown in FIG. 1 and FIG. 2. In addition, Table 3 and Table 4 show results of calculation of each similarity factor.

TABLE 3

| Similarity factor of Preparation A | |
|---|---|
| Comparison of Z515A01 and Z515A02 | 43 |
| Comparison of Z515A01 and Z515A03 | 29 |
| Comparison of Z515A02 and Z515A03 | 45 |

TABLE 4

| Similarity factor of Preparation B | |
|---|---|
| Comparison of Z515G01 and Z515G02 | 81 |
| Comparison of Z515G01 and Z515G03 | 98 |
| Comparison of Z515G02 and Z515G03 | 85 |

INDUSTRIAL APPLICABILITY

According to the present invention, a tablet showing regulated variation in dissolution of a hardly soluble active ingredient is obtained.

The invention claimed is:

1. A tablet containing about 3 to about 50% by weight (w/w) of (S)—N-[2-(1,6,7,8-tetrahydro-2H-indeno[5,4-b]furan-8-yl)ethyl]propionamide based on the whole tablet, magnesium stearate, and about 3% by weight (w/w) of hydroxypropylcellulose having a viscosity of about 1 to about 4 mPa·s based on the whole tablet.

* * * * *